(12) United States Patent
Grobler et al.

(10) Patent No.: US 10,363,324 B2
(45) Date of Patent: Jul. 30, 2019

(54) PHARMACEUTICAL COMPOSITION

(71) Applicants: The South African Nuclear Energy Corporation Limited, Brits Magisterial District (ZA); North-West University, Potchefstroom (ZA)

(72) Inventors: Anne Frederica Grobler, North West Province (ZA); Jan Rijn Zeevaart, Pelindaba (ZA)

(73) Assignees: The South African Nuclear Energy Corporation Limited, Brits Magisterial District (ZA); North-West University, Potchefstroom (ZA)

( * ) Notice: Subject to any disclaimer, the term of this patent is extended or adjusted under 35 U.S.C. 154(b) by 0 days.

(21) Appl. No.: 15/034,281

(22) PCT Filed: Nov. 4, 2014

(86) PCT No.: PCT/IB2014/065789
§ 371 (c)(1),
(2) Date: May 4, 2016

(87) PCT Pub. No.: WO2015/063746
PCT Pub. Date: May 7, 2015

(65) Prior Publication Data
US 2016/0271279 A1  Sep. 22, 2016

(30) Foreign Application Priority Data

Nov. 4, 2013 (ZA) .................................. 2013/08240
Jun. 20, 2014 (ZA) .................................. 2014/04551

(51) Int. Cl.
*A61K 51/12* (2006.01)
*A61K 9/00* (2006.01)
*A61K 47/02* (2006.01)
*A61K 47/12* (2006.01)
*A61K 47/14* (2017.01)
*A61K 9/107* (2006.01)

(52) U.S. Cl.
CPC .......... *A61K 51/122* (2013.01); *A61K 9/0019* (2013.01); *A61K 9/0053* (2013.01); *A61K 9/1075* (2013.01); *A61K 47/02* (2013.01); *A61K 47/12* (2013.01); *A61K 47/14* (2013.01); *A61K 51/1244* (2013.01)

(58) Field of Classification Search
CPC .......... A61K 9/00; A61K 47/02; A61K 47/12; A61K 51/122
See application file for complete search history.

(56) References Cited

U.S. PATENT DOCUMENTS

| 4,851,209 | A  | * | 7/1989  | Vasquez | ............ | A61K 51/0491 |
|           |    |   |         |         |              | 424/1.69     |
| 8,088,749 | B2 | * | 1/2012  | Simeone | ............ | A61K 31/7088 |
|           |    |   |         |         |              | 514/44 R     |
| 8,394,758 | B2 | * | 3/2013  | Wu      | ............ | C07K 7/08    |
|           |    |   |         |         |              | 424/1.69     |
| 2001/0018072 | A1 | * | 8/2001  | Unger | ............ | A61K 9/0009 |
|           |    |   |         |         |              | 424/484      |
| 2009/0304582 | A1 | * | 12/2009 | Rousso | ............ | A61B 5/02755 |
|           |    |   |         |         |              | 424/1.61     |

FOREIGN PATENT DOCUMENTS

| WO | 97/49335 A1 | 12/1997 |
| WO | 02/05849 A2 | 1/2002 |
| WO | 02/05850 A2 | 1/2002 |
| WO | WO 0205849 | * 1/2002 |
| WO | 2005042766 A2 | 5/2005 |
| WO | 2008135886 A2 | 11/2008 |
| WO | 2009004595 A2 | 1/2009 |
| WO | WO2009004595 | * 1/2009 |

OTHER PUBLICATIONS

International Search Report from International Application No. PCT/IB2014/065789, dated Jan. 21, 2015, 3 pages.
Swanepoel, Braam et al. "Tracing of the Pheroid®'s Bio-Distribution by Making Use of Radioactive 99MTC MDP.", Poster, Nov. 4-10, 2012, The Farm Inn Hotel, Pretoria, South Africa.
Swanepoel, Braam et al. "Enhanced Absorption of an Active Pharmaceutical Ingredient Through the Entrapment in the Pheroid System", Poster, Oct. 4-6, 2013, Academy of Pharmaceutical Science Conference 2013 Cape Town 4.

(Continued)

*Primary Examiner* — Michael G. Hartley
*Assistant Examiner* — Jagadishwar R Samala
(74) *Attorney, Agent, or Firm* — Meuiner Carlin & Curfman LLC

(57) ABSTRACT

This invention relates to a pharmaceutical composition for parenteral or oral administration containing a radioactive compound which can be used diagnostically or therapeutically. The composition comprises a micro-emulsion constituted by a dispersion of vesicles or microsponges of a fatty acid based component in an aqueous or other pharmacologically acceptable carrier in which nitrous oxide is dissolved, the fatty acid based component comprising at least one long chain fatty acid based substance selected from the group consisting of free fatty acids and derivatives of free fatty acids, and the radioactive compound.

6 Claims, 6 Drawing Sheets

(56) References Cited

OTHER PUBLICATIONS

Grobler, Paul et al. Abstract "Enhanced Absorption of the Radiotracer, (99MTC-MIBI) Through the Entrapment in the Pheroid System", Abstract, Jun. 24-26, 2013, The European Summit for Clinical Nanomedicine (CLINAM), Basel, Switzerland.
Grobler, Paul et al. "Enhanced Absorption of the Radiotracer, (99MTC-MIBI) Through Entrapment in the Pheroid System", Poster, Jun. 24-26, 2013, The European Summit for Clinical Nanomedicine (CLINAM), Basel, Switzerland.
Swanepoel, Braam et al. "Enhanced Absorption of an Active Pharmaceutical Ingredient Through the Entrapment in the Pheroid System", Abstract, Oct. 4-6, 2013, Academy of Pharmaceutical Science Conference 2013 Cape Town.

\* cited by examiner

PHARMACEUTICAL COMPOSITION

BACKGROUND OF THE INVENTION

THIS invention relates to a pharmaceutical composition containing a radioactive compound, also known as a radiopharmaceutical composition.

It is an object of this invention to provide an improved pharmaceutical composition containing a radioactive compound.

SUMMARY OF THE INVENTION

According to the present invention, there is provided a pharmaceutical composition for parenteral or oral administration containing a radioactive compound which can be used diagnostically or therapeutically, wherein the composition comprises a micro-emulsion constituted by a dispersion of vesicles or microsponges of a fatty acid based component in an aqueous or other pharmacologically acceptable carrier in which nitrous oxide is dissolved, the fatty acid based component comprising at least one long chain fatty acid based substance selected from the group consisting of free fatty acids and derivatives of free fatty acids, and the radioactive compound.

The radioactive compound may be selected from $^{99m}$Tc, $^{188}$Re, $^{186}$Re, $^{153}$Sm, $^{166}$Ho, $^{90}$Sr, $^{89}$Sr, $^{67}$Ga, $^{68}$Ga, $^{111}$In, $^{183}$Gd, $^{59}$Fe, $^{225}$Ac, $^{212}$Bi, $^{211}$At, $^{211}$At, $^{45}$Ti, $^{60}$CU, $^{61}$Cu, $^{67}$Cu, $^{64}$Cu, $^{62}$Cu, $^{195m}$Pt, $^{191m}$Pt, $^{193m}$Pt, $^{117m}$Sn, $^{103}$Pd, $^{103m}$Rh, $^{89}$Zr, $^{177}$Lu, $^{223}$Ra, $^{224}$Ra, $^{32}$P and $^{33}$P.

Preferably, the radioactive compound is labeled to a pharmaceutical compound, called a radiolabelled pharmaceutical compound, that transports it to a required location in the body after administration.

Examples of radiolabelled pharmaceutical compounds are: In-111 Oxyquinoline, Tc-99m Disofenin, Tc-99m Lidofenin, Tc-99m Mebrofenin, Tc-99m Disida, Sodium Chromate Cr-51, Sodium Pertechnetate Tc-99m, Iofetamine I-123, Sodium I-131, Sodium Fluoride F-18, Tc-99m Pyrophosphate, Tc-99m (Pyro- and trimeta-) Phosphates, Tc-99m Albumin Colloid, Tc-99m Sulfur Colloid, Fluodeoxyglucose F-18, In-111 Pentetreotide, Tc-99m Exametazime, Tc-99m Gluceptate, Tc-99m Arcitumomab, Tc-99m Nofetumomab Merpentan, Ferrous Citrate Fe-59, Tc-99m Teboroxime, Tc-99m Tetrofosmin, Thallous Chloride Tl-201, Iodohippurate Sodium I-123, Iodohippurate Sodium I-131, Iothalamate Sodium I-125, Tc-99m Succimer, Cyanocobalamin Co-57, Iobenguane, Sodium I-123, Iobenguane, Sodium I-131, F-18 florbetapir, F-18 florbetaben, F-18 NAV4694, F-18 Flutemetamol, I-123 Ioflupane, I-131 tositumomab, Sm-153 EDTMP, Ho-166 DOTMP, Re-186-HEDP, Sr-89 chloride Y-90 chloride, Y-90 ibritumomab tiuxetan, Re-188-HEDP, Tc-99m-HEDP, Zr-89 DFO-J549, Cu-64 ATSM, P-32 sodium phosphate, Ga-68 DOTATATE, Ga-68 RGD, Ga-68 UBI, Ga-68 citrate, Lu-177 DOTATATE, Lu-177 ibritumomab tiuxetan, Lu-177-EDTMP, F-18 maltose, F-18-maltohexaose, F-18-2-fluorodeoxy sorbitol, Pt-195m cisplatinum, Pt-195m carboplatinum, Pt-195m satraplatin, Pt-195m eloxatin, I-123 Deoxyuridine, I-125 Deoxyuridine, Technescan™ HDP (Tc-99m oxidronate), CARDIOLITE® (Tc-99m sestamibi), AN-DTPA® (Tc-99m Pentetate), Technescan™ MAG3 (Tc-99m mertiatide), Gluscan® (F-18 FDG), Xofigo® (Ra-223 Chloride), Gallium Citrate Ga-67 Injection.

A preferred radioactive compound is $^{99m}$Tc, and the preferred radiolabeled pharmaceutical is $^{99m}$Tc (medronic acid) MDP or $^{99m}$Tc-sestaMIBI (MIBI).

In one embodiment of the invention, the composition is for oral administration, typically in solution or in a capsule.

In the case where the composition is for oral administration, the composition may contain:
- 1 µl to 88 ml by volume water; preferably 1 to 10 ml, typically 2-5 ml;
- 100 µl to 1300 µl by volume fatty acid, preferably 0.5 to 1.2 ml, more preferably about 1 ml; and
- 370 kBq to 37 GBq radioactivity, preferably 100 to 500 MBq, typically 350-400 MBq.

In another embodiment of the invention, the composition may be for intravenous or intraperitoneal administration.

In the case where the composition is for intravenous injection, the composition may contain:
- 90 µl to 10 ml by volume water, preferably 1 to 5 ml, typically 2 to 3 ml;
- 10 µl to 3 ml by volume fatty acid, preferably 1 to 2 ml, more preferably about 1 ml; and
- 370 kBq to 37 GBq radioactivity, preferably 100 to 500 MBq, typically 350-400 MBq.

The composition is prepared by combining an aqueous formulation in which nitrous oxide is dissolved and containing fatty acid based component comprising at least one long chain fatty acid based substance selected from the group consisting of free fatty acids and derivatives of free fatty acids with an aqueous formulation containing a radioactive compound, and mixing with a high speed mixer, let stand for 45 minutes to an hour, and then administer the formulation.

The invention also covers a method of administering a radiolabelled pharmaceutical compound to a subject in need thereof, the method including the steps of providing a micro-emulsion constituted by a dispersion of vesicles or microsponges described above, mixing the dispersion with a composition containing a radiolabelled pharmaceutical, and administering the mixture to subject orally, intravenously or intraperitoneally in a diagnostic or therapeutic method of treatment.

DESCRIPTION OF PREFERRED EMBODIMENTS

Figure 1:
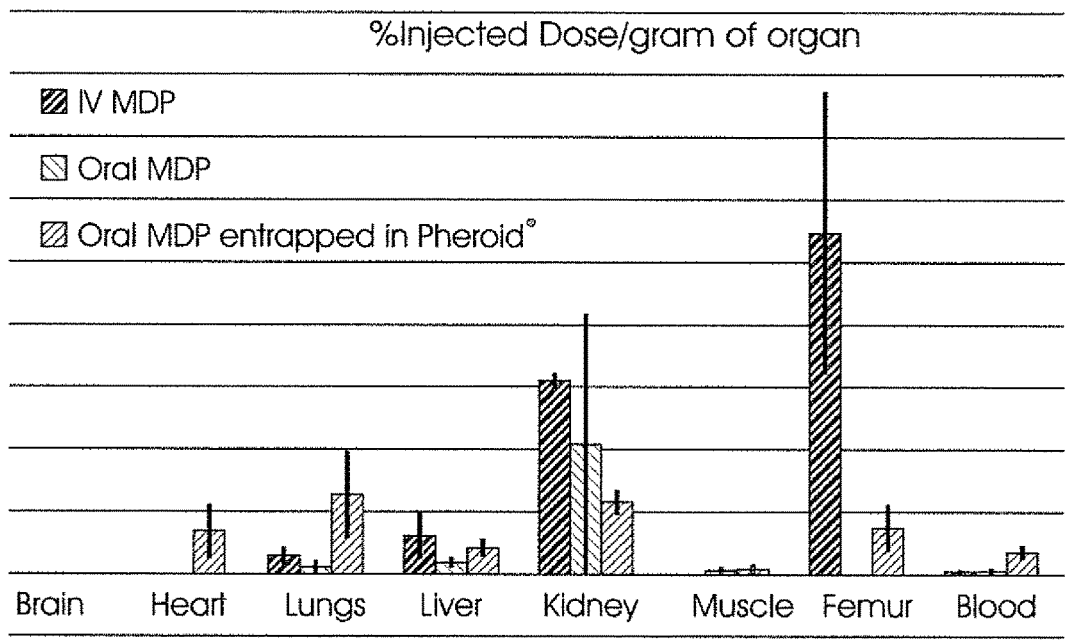
FIGS. 1-3 are graphs showing the results of bio-distribution, absorption, and blood results, respectively, of tests comparing compositions and administration routes using the radioactive tracer molecule $^{99m}$Tc MDP.

According to the present invention there is provided a pharmaceutical composition for parenteral or oral administration containing a radioactive compound such as, $^{188}$Re, $^{185}$Re, $^{153}$Sm, $^{166}$Ho, $^{90}$Sr, $^{89}$Sr, $^{67}$Ga, $^{68}$Ga, $^{111}$In, $^{183}$Gd, $^{59}$Fe, $^{225}$Ac, $^{212}$Bi, $^{211}$At, $^{211}$At, $^{45}$Ti, $^{60}$Cu, $^{61}$Cu, $^{67}$Cu, $^{64}$Cu, $^{62}$Cu, $^{195m}$Pt, $^{191m}$Pt, $^{193m}$Pt, $^{117}$Sn, $^{103}$Pd, $^{103m}$Rh, $^{89}$Zr, $^{177}$Lu, $^{223}$Ra, $^{224}$Ra, $^{32}$P and $^{33}$P, in particular $^{99m}$Tc.

The radioactive compound is labelled (i.e. tagged or bound to) a pharmaceutical compound to provide a radiopharmaceutical compound that transports it to a required location in the body after administration.

The composition comprises a micro-emulsion constituted by a dispersion of vesicles or microsponges of a fatty acid based component in an aqueous or other pharamacologically acceptable carrier in which nitrous oxide is dissolved, the fatty acid based component comprising at least one long chain fatty acid based substance selected from the group consisting of free fatty acids and derivatives of free fatty acids, and also an oxidant such as di-α-tocopherol, known as Pheroid® delivery system. Pheroid® technology comprises of a lipid bilayer constructed mainly of ethylated and pegylated poly unsaturated fatty acids. This drug delivery system has three phases, an oil, water and gas phase. Essential and plant fatty acids necessary for normal cell function, are dispersed in a water phase saturated with nitrous oxide ($N_2O$) to spontaneously form lipid structures. Pheroid® mainly consist of Vitamin F ethyl ester, Cremophor® EL, DL-α-tocopherol and nitrous oxide (Grobler, 2009). Vitamin F ethyl ester is an essential fatty acid. DL-α-tocopherol is an antioxidant and emulsion. Cremophor® EL is an excipient. Pheroid® can be manipulated in size and morphology to optimize therapeutic effect. The size is determined by the type, ratio and saturated state of the fatty acids as well as the manufacturing procedure.

The Pheroid® delivery system is a unique submicron emulsion-type formulation and consists of different types of Pheroid® formulations depending on the composition and manufacturing method (Uys, 2006). The formulations are:

1. Pheroid® vesicles.
2. Pheroid® microsponges.
3. Pro-Pheroid® in depots or reservoirs.

Pheroid® formulations consist of natural essential fatty acids diffuse in a liquid and nitrous oxide gas phase (Grobler et al., 2008). It may be applied as a delivery system to entrap, transport and deliver the active pharmaceutical ingredient (API) to a site of interest.

In the case of Pheroid® vesicles, the fatty acid based component may be selected from the group consisting of oleic acid, linoleic acid, alpha-linolenic acid, gamma-linolenic acid, and ricinoleic acid, and derivatives thereof selected from the group consisting of the Ci to C§ alkyl esters thereof, the glycerol-polyethylene glycol esters thereof, and the reaction product of hydrogenated and unhydrogenated natural oils composed largely of ricinoleic acid based oils with ethylene oxide.

In the case of Pheroid® microsponges, the microsponges may be constituted by the addition of long chain polyunsaturated fatty acids selected from eicosapentaenoic acid [C20 5ω3] and decosahexaenoic acid [C22 6ω3] or a mixture of both.

The vesicles or microsponges may be nano or micro size and in the form of a Pheroid® or Pro-Pheroid® consisting of fatty-acids and empty chamber(s) at the centre.

The Pro-Pheroid® can be with or without organic solvent such as ethanol but to a maximum of 10% v/v. Its benefit is that it will self-assemble in the stomach, entrap the API in situ and enhance the API uptake. The composition is therefore 2.8 to 100% fatty acids the latter being the Pro-Pheroid®. (In terms of the water phase i.e. 97.2% to 0% v/v). Also the Pheroid® formulations should contain tocopherol, minimum 0.1% and no more than 5% v/v. One could therefore reflect the fatty acid ranges as follows 2.8%-99.9% v/v. Furthermore the fatty acids may be in the form of ethyl esters thereof or short PEG (Polyethylene Glycol) esters thereof.

An embodiment of the invention relates to technetium which is a gamma emitter that has been used for many years as imaging agents. With its excellent physical characteristics and easy availability from a generator, technetium has become one of the most important nuclide for organ imaging in nuclear medicine (Subramanian at al., 1973).

There are 31 radiopharmaceuticals based on $^{99m}$Tc for imaging and functional studies of the brain, myocardium, thyroid, lungs, liver, gallbladder, kidneys, skeleton, blood, and tumors. (Schowchau, 2000) Depending on the procedure, the $^{99m}$Tc is labelled (tagged or bound to) a pharmaceutical that transports it to its required location. $^{99m}$Tc sestaMIBI (methoxyisobutylisonitrile—MIBI) is used for myocardial perfusion imaging, which shows how well the blood flows through the heart. Technetium-99m-sestaMIBI ($^{99m}$Tc-MIBI) is a small, lipophilic and cationic compound used for myocardial perfusion imaging. In addition, $^{99m}$Tc-MIBI has been shown to be useful in identifying several types of tumors, such as breast, lung and thyroid cancers (Tasdelen, 2011). $^{99m}$Tc-MIBI Injection is a myocardial perfusion agent that is indicated for detecting coronary artery disease by localizing myocardial ischemia (reversible defects) and infarction (non-reversible defects), in evaluating myocardial function and developing information for use in patient management decisions (Bouquillon at al., 1995). $^{99m}$Tc-MIBI evaluation of myocardial ischemia can be accomplished with rest and cardiovascular stress techniques. The product, under the brand name Cardiolite, is used commercially. Their targeting ability attracted considerable attention and as such a series of $^{99m}$Tc complexes of phosphonates were developed as bone imaging agents. Initially pyrophosphate was proposed but diphosphonates such as methylenediphosphonate (MDP) showed improved ability. MDP is taken up preferentially by bone attaching to the calcium ions on the hydroxyapatite bone surface. A fracture in the bone, for example, results in an increased physiological function and the tracer will accumulate in a significant concentration in this region appearing as a "hot spot" on the scan. (Dilworth et al, 1998) $^{99m}$Tc-bone scans are most frequently used to determine if a cancer patient has bone metastases. Metastatic tumours are common in the advanced stage of cancer. Prostate and breast cancer have been known to metastasize to bone. $^{99m}$Tc-bone scans can also provide information on lesions that cannot be identified using conventional X-ray methods as well as aid in the diagnosis of problems with joints such as the elbow and knee that are not easily detected using Magnetic Resonance Imaging (MRI).

It has, surprisingly, been found that the composition of the invention can be used for oral administration, typically in solution or in a capsule. Radiopharmaceuticals are usually prepared as injectable compositions. Injectable compositions have drawbacks, fear of needles and for patients undergoing chemotherapy as their arteries often collapse upon inserting a needle. The administration of radiopharmaceuticals in the composition of the present invention orally avoids these drawbacks.

Another unexpected aspect of the invention is that the Pheroid® delivery system of the present invention has unexpected advantages when use for intravenous or intraperitoneal administration. It has been found that accumulation of radiopharmaceuticals in the target organ are more than double when the radiotracer is entrapped inside the Pheroid® delivery system of the present invention as opposed to when the radiopharmaceutical is use as is. This will lead to better imaging of the organs. The clinical potential is exciting since diagnostic imaging plays a major role in enhanced diagnosis and clinical outcomes. This may also enable a decrease of the dosage of the given radiotracer and still get the desired results.

Examples of radiolabelled pharmaceutical compounds are: In-111 Oxyquinoline, Tc-99m Disofenin, Tc-99m Lidofenin, Tc-99m Mebrofenin, Tc-99m Disida, Sodium Chromate Cr-51, Sodium Pertechnetate Tc-99m, Iofetamine I-123, Sodium I-131, Sodium Fluoride F-18, Tc-99m Pyrophosphate, Tc-99m (Pyro- and trimeta-) Phosphates, Tc-99m Albumin Colloid, Tc-99m Sulfur Colloid, Fluodeoxyglucose F-18, In-111 Pentetreotide, Tc-99m Exametazime, Tc-99m Gluceptate, Tc-99m Arcitumomab, Tc-99m Nofetumomab Merpentan, Ferrous Citrate Fe-59, Tc-99m Teboroxime, Tc-99m Tetrofosmin, Thallous Chloride Tl-201, Iodohippurate Sodium I-123, Iodohippurate Sodium I-131, Iothalamate Sodium I-125, Tc-99m Succimer, Cyanocobalamin Co-57, Iobenguane, Sodium 1-123, Iobenguane, Sodium 1-131, F-18 florbetapir, F-18 florbetaben, F-18 NAV4694, F-18 Flutemetamol, I-123 loflupane, I-131 tositumomab, Sm-153 EDTMP, Ho-166 DOTMP, Re-186-HEDP, Sr-89 chloride Y-90 chloride, Y-90 ibritumomab tiuxetan, Re-188-HEDP, Tc-99m-HEDP, Zr-89 DFO-J549, Cu-64 ATSM, P-32 sodium phosphate, Ga-68 DOTATATE, Ga-68 RGD, Ga-68 UBI, Ga-68 citrate, Lu-177 DOTATATE, Lu-177 ibritumomab tiuxetan, Lu-177-EDTMP, F-18 maltose, F-18-maltohexaose, F-18-2-fluorodeoxy sorbitol, Pt-195m cis-platinum, Pt-195m carboplatinum, Pt-195m satraplatin, Pt-195m eloxatin, I-123 Deoxyuridine, I-125 Deoxyuridine, Technescan™ HDP (Tc-99m oxidronate), CARDIOLITE® (Tc-99m sestamibi), AN-DTPA® (Tc-99m Pentetate), Technescan™ MAG3 (Tc-99m mertiatide), Gluscan® (F-18 FOG), Xofigo® (Ra-223 Chloride), Gallium Citrate Ga-67 Injection.

Depending on the radiopharmaceutical, the Pheroid® composition of the invention may be used in methods of treatment or diagnosis in mammalian subjects and patients in need thereof.

In the case where the composition is for oral administration, the composition may contain 1 µl to 88 ml by volume water; 100 µl to 1300 µl by volume fatty acid; and 370 kBq to 37 GBq radioactivity.

In the case where the composition is for intravenous injection, the composition may contain 90 µl to 10 ml by volume water; 10 µl to 3.0 ml by volume fatty acid; and 370 kBq to 37 GBq radioactivity.

Radiopharmaceuticals can either be prepared in a central radiopharmacy or in house using a kit. In both cases the prepared formulation can be added to a vial containing Pheroid® enabling the Pheroid®-entrapped radiopharmaceutical to be orally administered or providing higher target organ uptake when administered intravenous or intraperitoneal. It is therefore proposed that an additional vial containing Pheroid® is provided for patients that need it. This can however also be performed in a central radiopharmacy, formulating the specific patient dose with addition of Pheroid® ready for administration. The ratio of the aqueous formulation containing a radioactive compound to formulation containing vesicles or microsponges, by weight, may be 1:5 to 1:10, typically 1:6 to 1:8.

The invention will be described in more detail with reference to the following Examples.

EXAMPLE 1

A Pheroid® formulation according to the invention may be made up as follows:

Step 1: A desired volume of water is saturated with nitrous oxide gas at ambient pressure using a pressure vessel and sparger. The vessel is connected to a supply of nitrous oxide via a flow control valve and pressure regulator. The closed vessel is supplied with nitrous oxide at a pressure of 2 bar for a period of 96 hours, it having been determined that at the aforementioned temperature the water is saturated with nitrous oxide over such period of time under the above-mentioned pressure. In the case of the preparation of the basic or stock formulation to be used as a carrier medium comprising a dispersion of vesicles unchlorinated water is used. The water is phosphate buffered to a pH of 5.8.

Step 2: The following fatty acid based compositions were made up: First, Vitamin F Ethyl Ester CLR 110 000 Sh.L. U./g obtained from CLR Chemicals Laboratorium Dr. Kurt Richter GmbH of Berlin, Germany which is composed mainly of 21% oleic acid, 34% linolenic acid, and 28% linoleic acid that are modified by esterification with an ethylene group of the carboxy terminal, was heated to 75° C. Secondly, pegylated, hydrogenated fatty acid, ricinoleic acid (also known by the INCI name as PEG-n-Hydrogenated Castor Oil), was heated to 80° C. and mixed with the first group of fatty acid based Vitamin F Ethyl Ester at 70° C. The ratio of the first group of fatty acids to the latter fatty acid was generally 2.8:1.

Step 3: di-a-Tocopherol of varying percentages (final concentration of between 0.1% when used as general anti-oxidant was added to the heated fatty acids mixture above.

Step 4: The buffered water was heated to 73° C. and mixed with the fatty acid mix with the aid of a high speed shearer to a final concentration of between 3.2 and 4%, depending on the specific use of the preparation. This fatty acid mixture constituted the basic preparation that contains vesicles of sizes in the nanometer range as determined by particle size analysis on a Malvern sizer.

This example of the invention involves the use of a radioactive tracer molecule $^{99m}$Tc MDP which is an effective bone tracer. An oral formulation is prepared by adding the Pheroide formulation (8 ml) to a prepared radiopharmaceutical (Tc-99m MDP)—water phase (2 ml). Mix with a mini blender for a few minutes. Let stand for an hour. Administer the formulation orally.

The radiopharmaceutical (Tc-99m MDP) water phase was prepared from a kit obtained from NTP Radioisotopes (Pty) Ltd. Each vial in the kit contains Methylene Diphosphonic Acid (5.00 mg), Tin Dichloride. 2 Hydrate (0.50 mg) and 2.5 Dihydroxybenzoic Acid (1.00 mg) in a sterile lyophilised form. The water phase was produced using Sodium Pertechnetate-Tc-99m with the sterile eluate of a Technetium-99m Generator.

In Vitro

Labelling Study

The labelling is a spontaneous process where technetium is just added to freeze dried MDP and after 5 minutes there should be labelling of 90% or higher. ITLC-SG plates were run in different mediums, Acetone and Saline. With the Saline medium the radioactivity should be transported from the point of origin or bottom to the top and for the Acetone it should stay at the bottom. Both cases delivered the required results which show that there was a 90 or higher percentage of labelling.

In Vivo

Control Study

An in vivo study was done to set positive and negative controls up for the full study where the Pheroid® system will be included. Sprague Dawley Rats was the chosen model for this study and they were divided into two groups of four rats each. In the first group $^{99m}$Tc MDP only was injected intravenously to serve as a positive control and demonstrate the natural distribution of the $^{99m}$Tc MDP. The second group served as the negative control and the $^{99m}$Tc MDP was administered orally, to reveal whether there was any absorption through the intestinal tract. The natural distribution was seen and zero absorption through the intestinal tract was reported.

Entrapment Study

Due to the radioactive nature of the product, traditional methods in which the onset of entrapment could be tested could not be used. After the control rat study was completed it was ascertained that there was zero oral absorption of the product and therefore a test was devised where the time for optimal entrapment could be gained. Several formulations were produced and given different time periods for entrapment of the product to occur. The formulation was then administered to rats and they were all sacrificed after one hour. The rat and time unit where the blood radioactive levels were the highest pointed to the optimal time for entrapment of the drug. This optimal time for entrapment was 24 hours.

Stability Study

After the entrapment test was compiled a stability/labelling test had to be done to see whether the $^{99m}$TC-MDP was still stable and the amount of labelled product was still high. This test was run in the same manner as the labelling test and the results were positive and the product still stable after 24 hours.

In Vivo

Bio-Distribution Study

The study contained 3 study groups of 12 animals each. A number of animal models may be used, including those of guinea pigs, rabbits, rats, mice, and non-human primates. In this study, the rat was the proposed model, since rats are relatively inexpensive, available and easy to handle. It was decided not to use mice, since the volume of labelled Pheroid® that can be administered and the resultant level of radioactivity in the various organs may be too low for detection.

The following treatments were administered to the 3 respective treatment groups.

1. $^{99m}$Tc-MDP alone per os.
2. $^{99m}$Tc-MDP entrapped in Pheroid® vesicles per os.
3. $^{99m}$Tc-MDP alone intravenously.

In Vivo

Imaging Study

In this part of the study 4 rats were used. In 3 rats the $^{99m}$Tc-MDP, entrapped in Pheroid® vesicles, was administered orally (per os, po) and the other 1 served as a control, where $^{99m}$Tc-MDP was also administered orally, but not entrapped in the Pheroid® system. With all 4 of the rats a static scan was done at 0, 60, 120 and 240 minutes. After the 240 minutes the rats were sacrificed and the organs harvested and counting will be done via a Capintec Beta Detector CRC®-Ultra Dose Calibrator and a Triathler™ NaI Well Counter on the organs.

Results

Bio-Distribution

The results are shown in Table 1 and FIG. 1. The bio-distribution was very interesting, with marked differences in the three systems. The Pheroid® system enabled conveyance of the drug, which was not absorbed in intestinal tract under normal circumstances, into the blood circulation through oral administration. The drug levels in the blood circulation are an adequate amount to compete with intravenous administration levels and the Pheroid® system also changed the normal distribution of the radiotracer $^{99m}$Tc MDP after intravenous administration.

TABLE 1

Results of bio-distribution study

| Control | IV % ID | STD | Oral % ID | STD | Pheroid | Oral % ID | STD |
|---|---|---|---|---|---|---|---|
| Brain | 0 | 0 | 0 | 0 | Brain | 0 | 0 |
| Heart | 0 | 0 | 0 | 0 | Heart | 0.068484 | 0.041831 |
| Lungs | 0.03081 | 0.012681 | 0.012171 | 0.008721 | Lungs | 0.127441 | 0.069072 |
| Liver | 0.062323 | 0.035975 | 0.01969 | 0.007286 | Liver | 0.043662 | 0.011758 |
| Kidney | 0.309884 | 0.011414 | 0.208924 | 0.208924 | Kidney | 0.115782 | 0.018717 |
| Muscle | 0 | 0 | 0.00451 | 0.00451 | Muscle | 0.007629 | 0.007629 |
| Femur | 0.54454 | 0.225466 | 0 | 0 | Femur | 0.073721 | 0.036861 |
| Blood | 0.004151 | 0.0025 | 0.005007 | 0.005007 | Blood | 0.035527 | 0.009767 |

Enhanced Absorption

Figure 2:
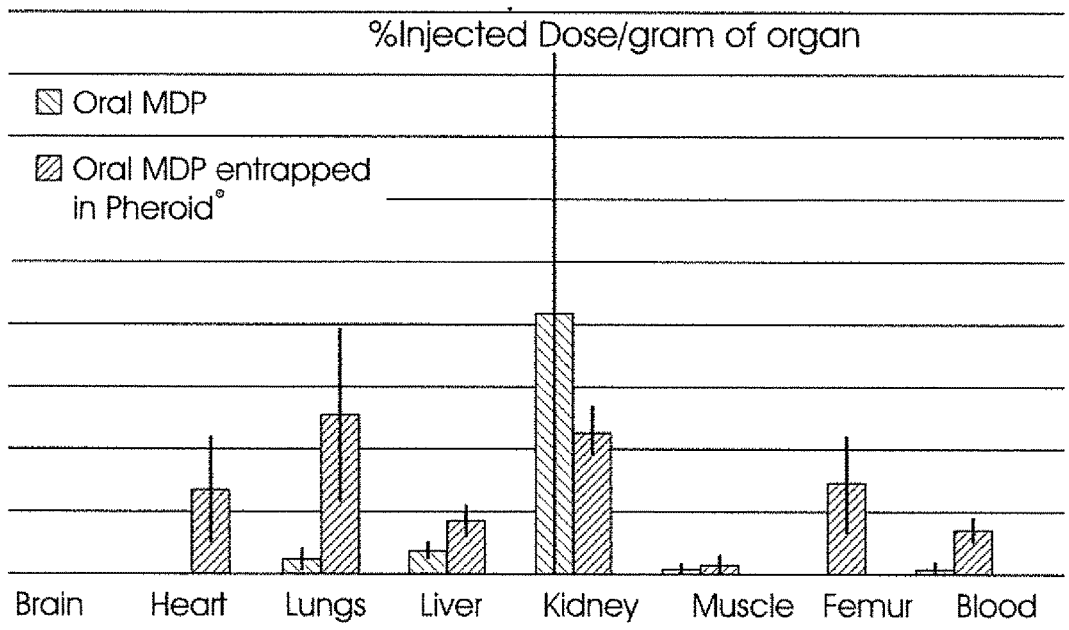

The results are shown in Table 2 and FIG. 2. Excellent oral absorption of the Pheroid® entrapped $^{99m}$Tc MDP through the intestinal tract was seen in contrast to little or zero absorption of the compound not entrapped in the Pheroid® vesicles. The Pheroid® is therefore directly responsible for the absorption. High levels of the $^{99m}$Tc MDP was seen in the lungs, liver and blood, which are key areas in infection treatment regimes.

TABLE 2 results of absorption study

| Control | Oral % ID | STD | Pheroid | Oral % ID | STD |
|---|---|---|---|---|---|
| Brain | 0 | 0 | Brain | 0 | 0 |
| Heart | 0 | 0 | Hart | 0.068484 | 0.041831 |
| Lungs | 0.012171 | 0.008721 | Lungs | 0.127441 | 0.069072 |
| Liver | 0.01969 | 0.007286 | Liver | 0.043662 | 0.011758 |
| Kidney | 0.208924 | 0.208924 | Kidney | 0.115782 | 0.018717 |
| Muscle | 0.00451 | 0.00451 | Muscle | 0.007629 | 0.007629 |
| Femur | 0 | 0 | Femur | 0.073721 | 0.036861 |
| Blood | 0.005007 | 0.005007 | Blood | 0.035527 | 0.009767 |

Blood Results

Figure 3:
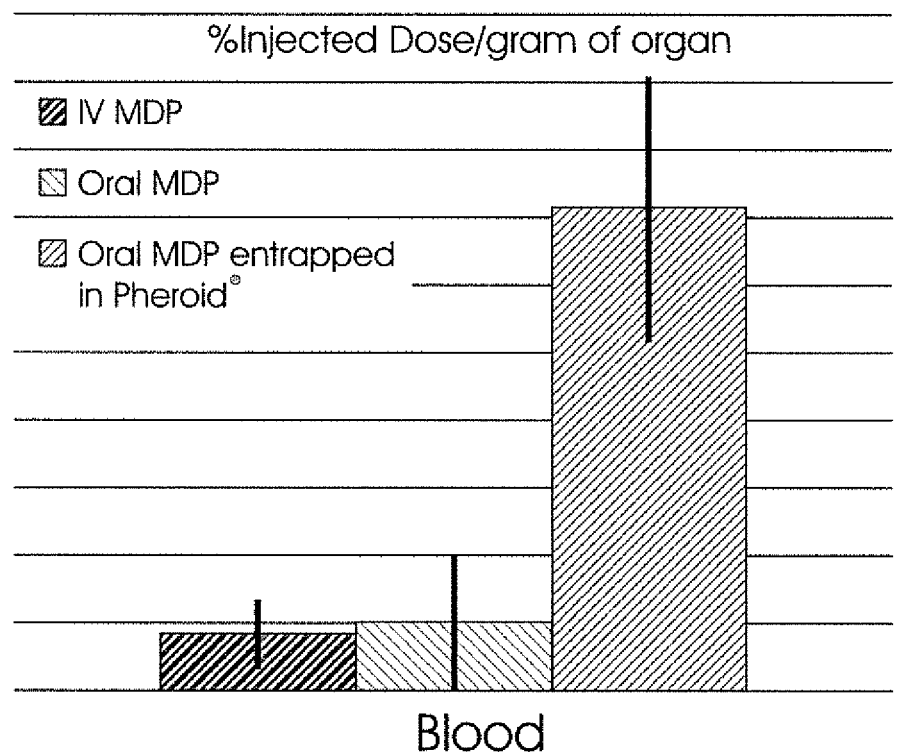

The results are shown in Table 3 and FIG. 3. Prolonged stay of the compound in the blood after four hours, after oral administration of the Pheroid® encapsulated compound, compared to very low levels after IV and oral administration without the help of the Pheroid® vesicles. The prolonged stay of the compound in the blood would mean increased half lives of drugs and therefore decrease administration frequencies.

TABLE 3

| Control | IV % ID | STD | Oral % ID | STD | Pheroid | Oral % ID | STD |
|---|---|---|---|---|---|---|---|
| Blood | 0.004151 | 0.0025 | 0.005007 | 0.005007 | Blood | 0.035527 | 0.009767 |

The capacity of the Pheroid® system to convey the radiopharmaceutical, which is not absorbed in the intestinal tract under normal conditions, into the blood circulation through oral administration is most surprising. In addition, the unexpected prolonged stay of the drug in the blood circulation will increase the half-life of the drug. This will be helpful in both administration regimes and diseases where blood is the infected area.

Figure 4:
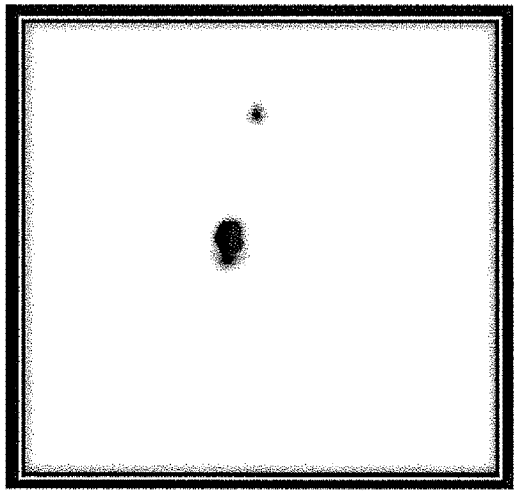
FIGS. 4-11 are images showing the results of tests comparing compositions and administration routes using the radioactive tracer molecule $^{99m}$Tc MDP.
Figure 5:
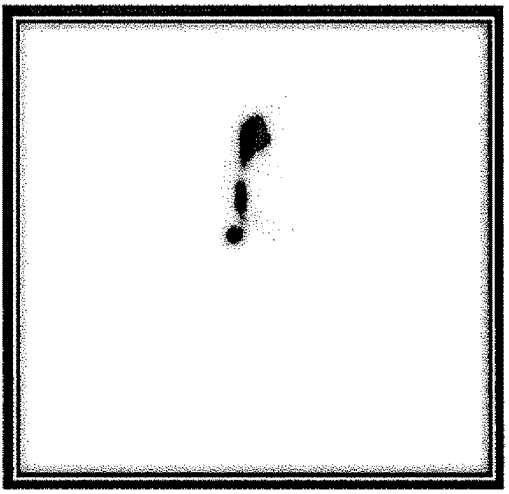
Figure 6:
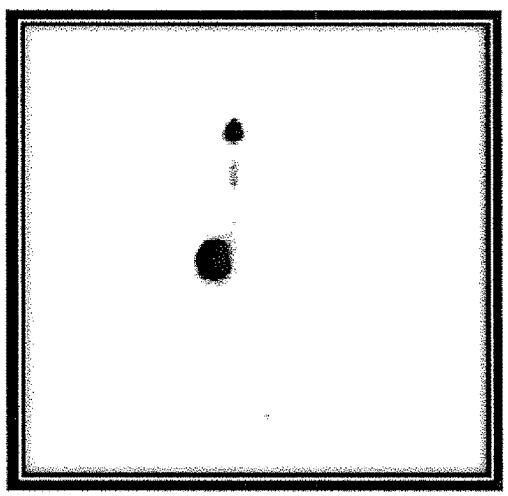
Figure 7:
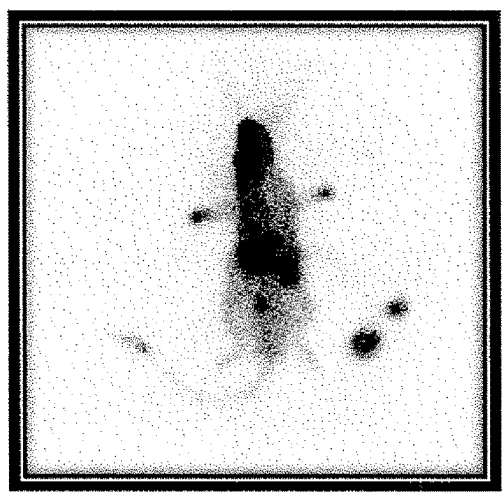
Figure 8:
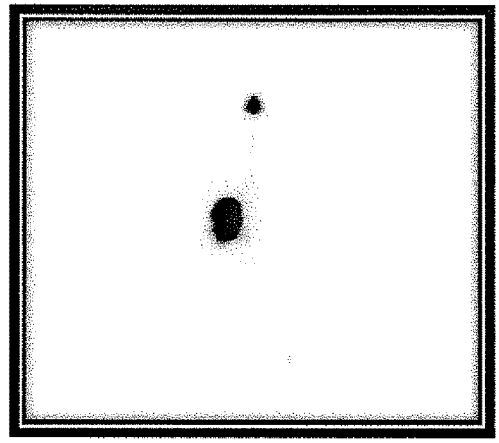
Figure 9:
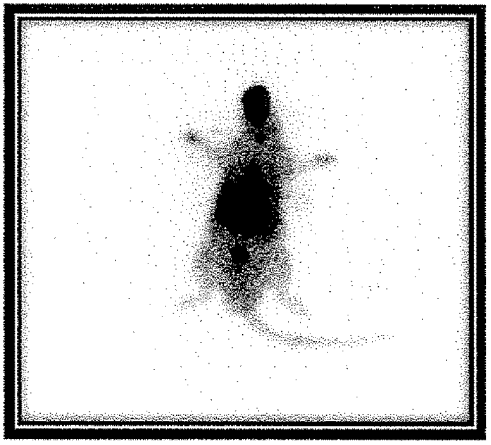
Figure 10:
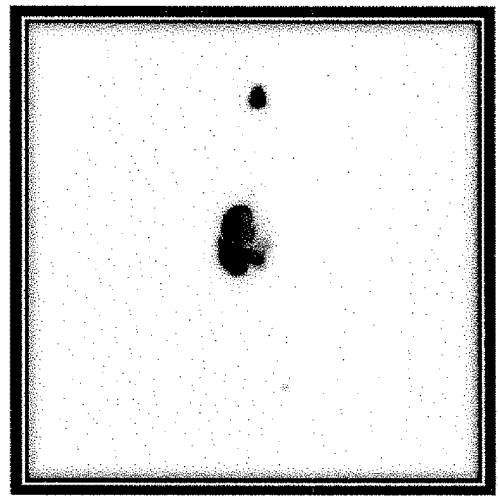
Figure 11:
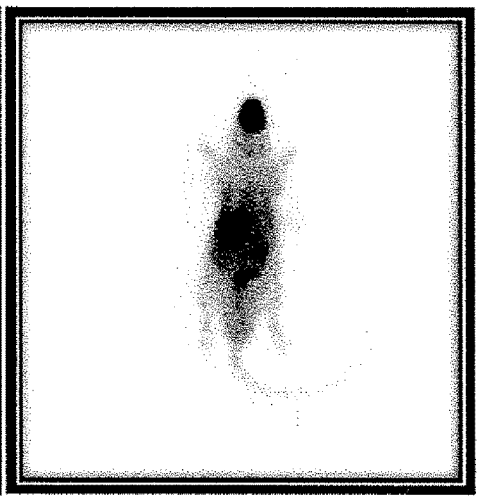

Imaging results are shown in FIGS. 4-11. FIG. 4 is an image at time zero, directly after administration of MDP labelled with Technetium. FIG. 5 is an image at time zero, directly after administration of MDP labelled with Technetium entrapped in the Pheroid® system. FIG. 6 is an image 1 hour after administration of MDP labelled with Technetium. FIG. 7 is an image 1 hour after administration of MDP labelled with Technetium entrapped in the Pheroid® system. FIG. 8 is an image 2 hours after administration of MDP labelled with Technetium. FIG. 9 is an image 2 hours after administration of MDP labelled with Technetium entrapped in the Pheroid® system. FIG. 10 is an image 4 hours after administration of MDP labelled with Technetium. FIG. 11 is an image 4 hours after administration of MDP labelled with Technetium entrapped in the Pheroid® system.

At time zero or directly after administration the images are very comparable. This is to be expected since no time has passed for absorption to take place. However at the other time points the difference in absorption and body distribution can easily be seen. Where the $^{9am}$Tc MDP has been administered on its own there is no absorption from the intestinal tract, however where the $^{99m}$Tc MDP has been entrapped within the Pheroid® system the absorption and body-distribution is easily spotted.

The capacity of the Pheroid® system to convey the drug, which is not absorbed in intestinal tract under normal conditions, into the blood circulation through oral administration is especially exciting since there are number of drugs that can only be administered intravenously, due to a lack of absorption through the gut. It will also be capable to help drugs that struggle with low absorption, which would lead to lowered cost and less side-effects.

The prolonged stay of the drug in the blood circulation would increase the half-life of the drug. This will then be helpful in both administration regimes and diseases where the blood is the infected area.

The ability of the Pheroid® system to change the biodistribution of a drug could also be incredibly helpful, particularly in drugs where side-effects are due to the drug acting in areas that is not of interest to the infection.

EXAMPLE 2

This example involves the use of a radioactive tracer molecule $^{99m}$Tc-MIBI. $^{99m}$Technetium-MIBI is used for myocardial imaging. $^{99m}$Tc-MIBI Injection is a myocardial perfusion agent that is indicated for detecting coronary artery disease by localizing myocardial ischemia (reversible defects) and infarction (non-reversible defects), in evaluating myocardial function and developing information for use in patient management decisions (Sun et al., 2003). $^{99m}$Tc-MIBI evaluation of myocardial ischemia can be accomplished with rest and cardiovascular stress techniques. It is usually not possible to determine the age of a myocardial infarction or to differentiate a recent myocardial infarction from ischemia.

An oral formulation was prepared by adding 8 ml the Pheroid® formulation (as per Example 1) to a prepared radiopharmaceutical (Tc-99m MIBI)—water phase (2 ml). Mix with a mini blender for a few minutes. Let stand for an hour. Administer the formulation orally.

The radiopharmaceutical (Tc-99m MIBI) water phase was prepared from a kit called Cariolite® obtained from Bristol-Myers Squibb. Each 5 ml vial in the kit contains a sterile, non-pyrogenic, lyophilised mixture of Tetrakis (2-methoxy isobutyl isonitrile Copper (I) tetrafluoroborate (1.0 mg), Sodium Citrate Dihydrate (2.6 mg), L-Cysteine Hydrochloride Monohydrate (1.0 mg), Mannitol (20 mg), Stannous Chloride, Dihydrate, minimum SnCl2.2H2O (0.025 mg), Stannous Chloride, Dihydrate, minimum SnCl2.2H2O (0.055 mg) and Tin Chloride (stannous and stannic) Dihydrate, maximum (as SnCl2.2H2O) (0.086 mg). The water phase was produced using Sodium Pertechnetate-Tc-99m with the sterile eluate of a Technetium-99m Generator.

Figure 12:
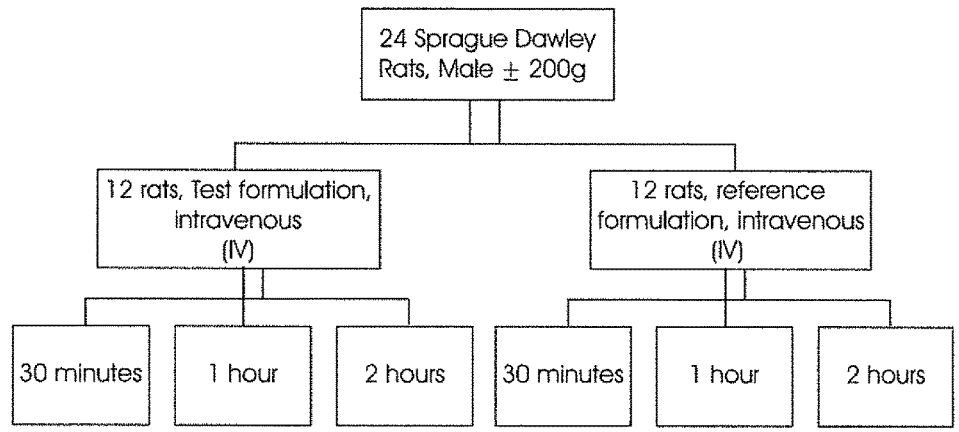
FIG. 12 is a schematic diagram showing the study design for tests comparing compositions administered intravenously using the radiotracer $^{99m}$Tc-MIBI.

In this study the intravenous administration of the radiotracer were investigated. The test formulation is defined for the purpose of this study as the radiotracer $^{99m}$Tc-MIBI entrapped in the Pheroid® system and the reference formulation as non-entrapped radiotracer. The comparative study design included twenty-four Sprague Dawley Rats. As shown in the FIG. 1 below, twelve animals each received the test and reference formulations respectively. These two groups of 12 rats were then divided into three groups of four rats each. Each of these groups was sacrificed at different time intervals (30 minutes, 1 and 2 hours) after administration. All organs were harvested and radioactivity of 14 organs were determined for each animal using a Capintec Beta Detector CRC®-Ultra Dose Calibrator and a Triathler™ NaI Well Counter. A schematic representation of the study design is shown in FIG. 12.

Figure 13:
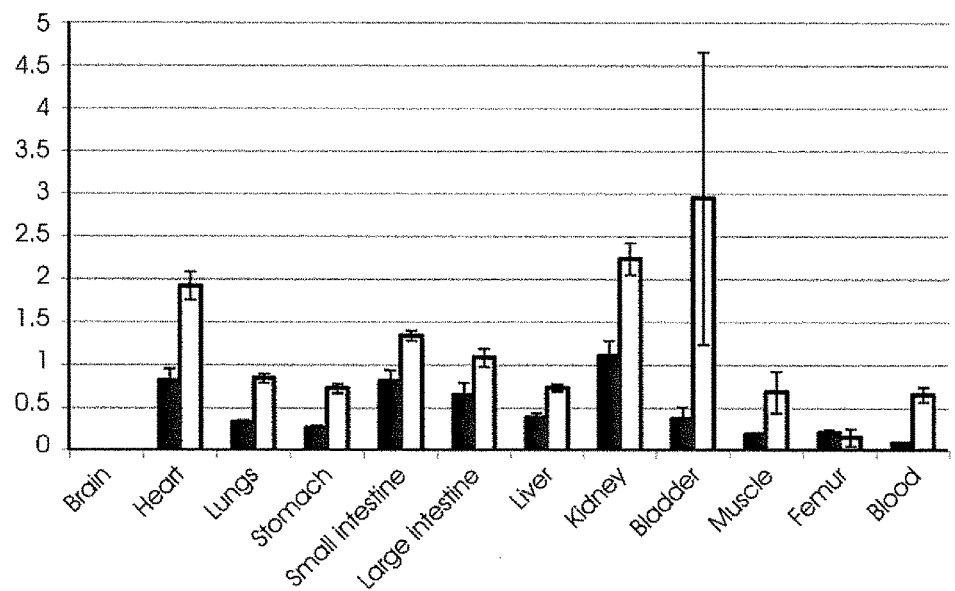
FIGS. 13-15 are graphs showing the results of tests comparing compositions administered intravenously using the radiotracer $^{99m}$Tc-MIBI.
Figure 14:
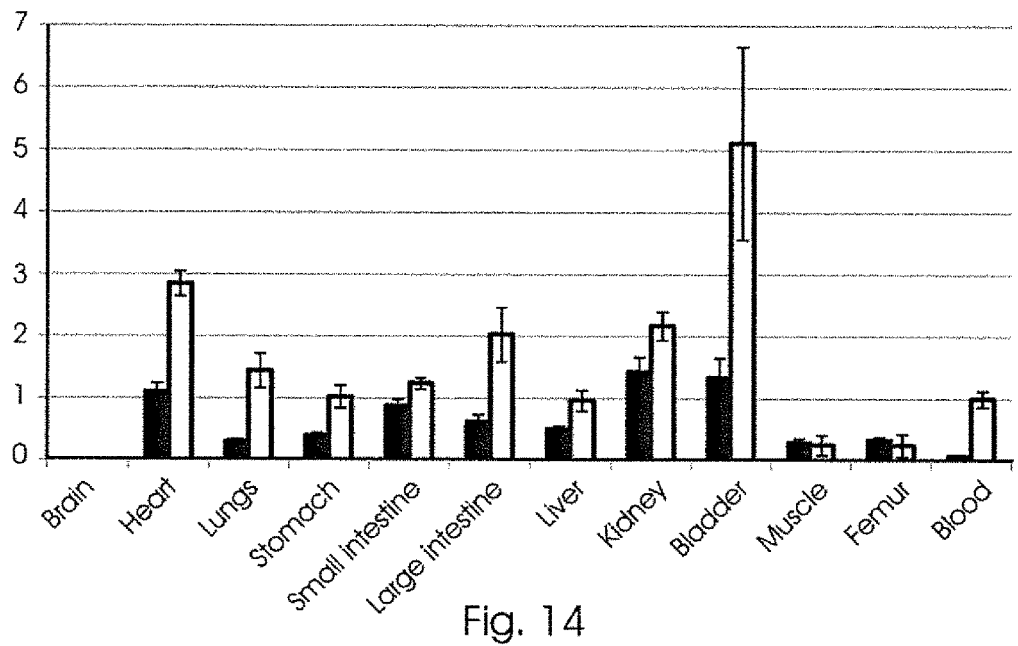
Figure 15:
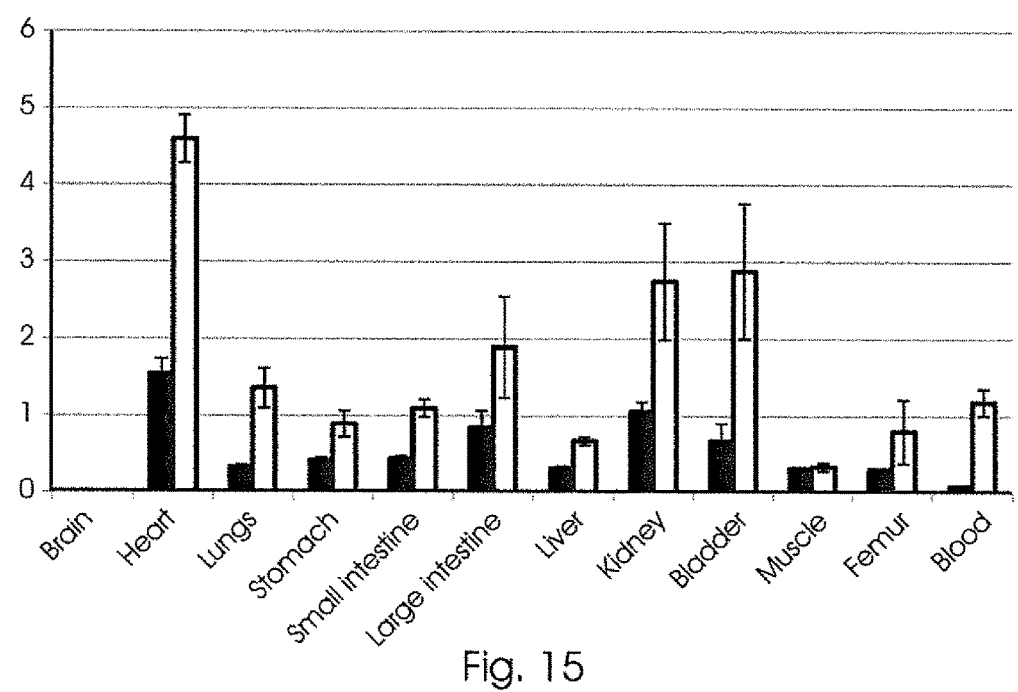

FIGS. 13-15 illustrate the percentage of the injected dose per gram of organ after IV administration of the test and reference formulation respectively.

FIG. 13 shows the percentage of injected dose per gram of organ. Data depicted as mean±SE of reference (black) and test (clear) formulations. Rats were sacrificed 30 minutes after administration.

The total body accumulation of the test formulation is more than double of that of the reference formulation. This means that the Pheroid® system enhanced absorption of the radiotracer and this will lead to better imaging of the desired organs.

FIG. 14 shows the percentage of injected dose per gram of organ. Data depicted as mean±SE of reference (black) and test (clear) formulations. Rats were sacrificed 1 hour after administration.

Accumulation of the drug levels in the heart are more than double when the radiotracer is entrapped inside the Pheroid® delivery system. This may enable a decrease of the dosage of the given radiotracer and still get the desired results. This result was even more pronounced 2 hours after administration as shown in FIG. 15.

FIG. 15 shows the percentage of injected dose per gram of organ. Data depicted as mean±SE of reference (black) and test (clear) formulations. Rats were sacrificed 2 hours after administration.

Entrapment of the radiotracer in the Pheroid® delivery system results in a statistically significant increase in the accumulation of the radiotracer in the target organ; in this case the heart. This will lead to better imaging of the organs. The clinical potential is exciting since diagnostic imaging plays a major role in enhanced diagnosis and clinical outcomes.

FIGS. 13-15 show a surprising result that the Pheroid® delivery system improves the delivery of the radiotracer when administered intravenously over reference formulations and the potential of using the formulation for administration of radiopharmaceuticals intravenously.

The data showed that the Pheroid® enhanced the availability of the Tc-MIBI in heart and blood. MIBI is used to image the heart. This means more Tc-MIBI reaches the heart and therefore this enhancement will require less of the Tc-MIBI (radiopharmaceutical) to obtain the same contrast (target to non-target) as is currently the practise. This will result in cost saving.

The following documents are incorporated herein by reference:

GROBLER, A. F., KOTZE, A. F., DU PLESSIS, J. 2008. The Design of a Skin-Friendly Carrier for Cosmetic Compounds Using Pheroid Technology. Science and Applications of Skin Delivery Systems. *Ed J Wiechers*. Allure Publications: 413-458.

GROBLER, A. F. 2009. Pharmaceutical applications of Pheroid™ technology. Published. PhD dissertation, North-West University.

KATZUNG, B. G. 2001. Basic & clinical pharmacology (8th ed.). San Francisco: The McGraw-Hill companies, Inc.

SAUNDERS, J. C. J., DAVIS, H. J., COETZEE, L., BOTHA, S., KRUGER, A. E. & GROBLER, A. 1999. A novel skin penetration enhancer: evaluation by membrane diffusion and con focal microscopy. *Journal of pharmacy and pharmaceutical sciences*, 2:99-107.

SUBRAMANIAN, G., MCAFFEE, J. G., BLAIN, R. J., KALLFELZ, F. A. 1973. $^{99m}$Tc-MDP (Methylene Diphosphonate): a superior agent for skeletal imaging. *Journal of Nuclear Medicine* 14: 640.

UYS, C. E. 2006. Preparation and characterization of Pheroid vesicles. Potchefstroom: NWU. (Dissertation-M.Sc). 147p.

SUN, Y., MA, P., BAX, J. J., BLOM, N., YU, Y., WANG, Y., HAN, X., WANG, Y., VAN DER WALL, E. E. 99m Tc-MIBI myocardial perfusion imaging in myocarditis. (Nuci Med Commun. 2003 July; 24(7):779-83).

Schwochau, Klaus (2000). Technetium: Chemistry and Radiopharmaceutical Applications. New York: Wiley. ISBN 3-527-29496-1. Dilworth, J. R. & Parrott, S. J. 1998. Chemical Society Reviews, 27:43-55.

The invention claimed is:

1. A method of administering a radiolabelled pharmaceutical compound to a subject in need thereof, the method including the steps of: providing a micro-emulsion constituted by a dispersion of vesicles or microsponges of a fatty acid based component in an aqueous or other pharmacologically acceptable carrier in which nitrous oxide is dissolved, the fatty acid based component comprising at least one long chain fatty acid based substance selected from the group consisting of oleic acid, linoleic acid, alpha-linolenic acid, gamma-linolenic acid, ricinoleic acid, eicosapentaenoic acid [C20 5ω3], and decosahexaenoic acid [C22 6ω3] and derivatives thereof selected from the group consisting of the C1 to C6 alkyl esters thereof, the glycerol-polyethylene glycol esters thereof, and a reaction product of hydrogenated and unhydrogenated natural oils comprising ricinoleic acid based oils with ethylene oxide, mixed with a composition containing a radiolabelled pharmaceutical compound comprising a radioactive compound labelled to a pharmaceutical compound wherein the radioactive compound is selected from $^{99m}$Tc, $^{188}$Re, $^{186}$Re, $^{153}$Sm, $^{166}$Ho, $^{90}$Sr, $^{89}$Sr, $^{67}$Ga, $^{68}$Ga, $^{111}$In, $^{183}$Gd, $^{59}$Fe, $^{225}$Ac, $^{212}$Bi, $^{211}$At, $^{211}$At, $^{45}$Ti, $^{60}$Cu, $^{61}$Cu, $^{67}$Cu, $^{64}$Cu, $^{62}$Cu, $^{195m}$Pt, $^{191m}$Pt, $^{193m}$Pt, $^{117m}$Sn, $^{103}$Pd, $^{103m}$Rh, $^{89}$Zr, $^{177}$Lu, $^{223}$Ra, $^{224}$Ra, $^{32}$P and $^{33}$P, and administering the mixture to the subject orally in a diagnostic or therapeutic method of treatment, wherein the radiolabelled pharmaceutical compound is absorbed through an intestinal tract of the subject and is transported to a required location in the body after administration where the radiolabelled pharmaceutical compound has a diagnostic or therapeutic effect.

2. The method of claim 1, wherein the mixture is left to stand for 45 minutes to 1 hour, prior to administration of the composition to the subject.

3. The method of claim 1, wherein the radiolabelled pharmaceutical compound is a compound selected from: In-111 Oxyquinoline, Tc-99m Disofenin, Tc-99m Lidofenin, Tc-99m Mebrofenin, Tc-99m Disida, Iofetamine I-123, Tc-99m Pyrophosphate, Tc-99m (Pyro- and trimeta-) Phosphates, Tc-99m Albumin Colloid, Tc-99m Sulfur Colloid, Fluodeoxyglucose F-18, In-111 Pentetreotide, Tc-99m Exametazime, Tc-99m Gluceptate, Tc-99m Arcitumomab, Tc-99m Nofetumomab Merpentan, Ferrous Citrate Fe-59, Tc-99m Teboroxime, Tc-99m Tetrofosmin, Thallous Chloride Tl-201, Iodohippurate Sodium I-123, Iodohippurate Sodium I-131, Iothalamate Sodium I-125, Tc-99m Succimer, Cyanocobalamin Co-57, Iobenguane, Sodium I-123, Iobenguane, Sodium I-131, F-18 florbetapir, F-18 florbetaben, F-18 NAV4694, F-18 Flutemetamol, I-123 Ioflupane, I-131 tositumomab, Sm-153 EDTMP, Ho-166 DOTMP, Re-186-HEDP, Sr-89 chloride Y-90 chloride, Y-90 ibritumomab tiuxetan, Re-188-HEDP, Tc-99m-HEDP, Zr-89 DFO-J549, Cu-64 ATSM, P-32 sodium phosphate, Ga-68 DOTATATE, Ga-68 RGD, Ga-68 UBI, Ga-68 citrate, Lu-177 DOTATATE, Lu-177 ibritumomab tiuxetan, Lu-177-EDTMP, F-18 maltose, F-18-maltohexaose, F-18-2-fluorodeoxy sorbitol, Pt-195m cisplatinum, Pt-195m carboplatinum, Pt-195m satraplatin, Pt-195m eloxatin, I-123 Deoxyuridine, I-125 Deoxyuridine, Technescan™ HDP (Tc-99m oxidronate), CARDIOLITE® (Tc-99m sestamibi), AN-DTPA® (Tc-99m Pentetate), Technescan™ MAG3 (Tc-99m mertiatide), Gluscan® (F-18 FDG), Xofigo® (Ra-223 Chloride), or Gallium Citrate Ga-67 Injection.

4. The method of claim 1, wherein the radioactive compound is $^{99m}$Tc.

5. The method of claim 4, wherein the radioactive compound is labelled to a pharmaceutical compound selected from $^{99m}$Tc (medronic acid) MDP or $^{99m}$Tc-sestaMIBI (MIBI).

6. The method of claim 1, wherein the mixture administered to the subject orally comprises:
 1 µl to 88 ml by volume water;
 100 µl to 1300 µl by volume fatty acid, and
 370 kBq to 37 GBq radioactivity.

* * * * *